(12) United States Patent
Bunn et al.

(10) Patent No.: US 6,344,189 B1
(45) Date of Patent: Feb. 5, 2002

(54) USE OF PROTEASE INHIBITORS FOR TREATING SKIN WOUNDS

(75) Inventors: Clive Leighton Bunn, West Ryde; John Lewis Andrews, Berowra; Phillip John Sharp, Glebe, all of (AU)

(73) Assignee: Biotech Australia Pty., Ltd., Roseville (AU)

( * ) Notice: Subject to any disclaimer, the term of this patent is extended or adjusted under 35 U.S.C. 154(b) by 0 days.

(21) Appl. No.: 09/190,451

(22) Filed: Nov. 13, 1998

Related U.S. Application Data
(60) Provisional application No. 60/084,682, filed on May 7, 1998, and provisional application No. 60/080,315, filed on Apr. 1, 1998.

(51) Int. Cl.[7] .............................................. A61K 31/74
(52) U.S. Cl. ...................... 424/78.06; 424/400; 510/12; 510/781; 510/944; 530/381
(58) Field of Search .............................. 424/78.06, 400; 514/781, 944, 12; 530/381

(56) References Cited

U.S. PATENT DOCUMENTS

| | | | |
|---|---|---|---|
| 5,202,118 A | 4/1993 | Gillis et al. | 424/85.2 |
| 5,298,400 A | * 3/1994 | Whitfeld et al. | 435/69.8 |
| 5,362,857 A | 11/1994 | Hock | 530/395 |
| 5,444,153 A | 8/1995 | Goss et al. | 424/141 |
| 5,599,788 A | 2/1997 | Purchio et al. | 514/2 |
| 5,646,117 A | 7/1997 | Matsushima et al. | 514/12 |
| 5,679,350 A | 10/1997 | Jankun et al. | 424/193.1 |
| 5,693,332 A | 12/1997 | Hansbrough | 424/426 |
| 5,821,220 A | * 10/1998 | Beaulieu et al. | 514/8 |
| 5,989,576 A | * 11/1999 | Fuller | 424/401 |

OTHER PUBLICATIONS

Stacey et al. Tissue and urokinase plasminogen activators in the environs of venous and ischemic leg ulcers. Br. J. Surg. vol. 80(5), pp. 596–599, 1993.*

Wlaschek et al. Protease inhibitors protect growth factor activity in chronic wounds. Correspondence. Br. J. Dermatology, vol. 137, p. 646, 1997.*

Serine protease inhibitors profiles distinguish chronic from acute wounds. Krishna et al. J. Invest. Dermatol. vol. 108(4), page. 617. Abstract submitted at the Annual Meeting of the Society for Investigative Dermatology, Washington, D.C., Apr. 23–27, 1997.*

Paloahti, M., et al., "Proteolytic Activity in Leg Ulcer Exudate," Experimental Dermatology, vol. 2, pp. 29–37 (1993).

Wysocki, A., et al., "Wound Fluid from Chronic Leg Ulcers Contains Elevated Levels of Metalloproteinases MMP–2 and MMP–9," Journal of Investigative Dermatology, vol. 101, No. 1, pp. 64–68 (Jul. 1993).

Kruithof, E., et al., "Biological and Clinical Aspects of Plasminogen Activator Inhibitor Type 2," Blood, vol. 86, No. 11, pp. 4007–4024 (Dec. 1995).

Matuszewska, B., et al., "Acidic Fibroblast Growth Factor Evaluation of Topical Formulations in a Diabetic Mouse Wound Healing Model," Pharmaceutical Research, vol. 11, No. 1, pp. 65–71 (1994).

Shahrokh, Z., et al., "Cellulose–Cleaving Activity Contaminating E. coli–Produced Recombinant Proteins," BioPharm, pp. 32–38 (Mar. 1995).

Tsai, P.K., et al., "Formulation Design of Acidic Fibroblast Growth Factor," Pharmaceutical Research, vol. 10, No. 5, pp. 649–659 (1993).

* cited by examiner

*Primary Examiner*—Thurman K. Page
*Assistant Examiner*—Lakshmi Channavajjala
(74) *Attorney, Agent, or Firm*—Foley & Lardner (57) ABSTRACT

The healing of chronic wounds, such as leg ulcers, is accelerated via topical administration of a serine protease inhibitor, such as PAI-2. Wound healing also is promoted using combinations of protease inhibitors, such as PAI-2 with other serine protease inhibitors and/or with protease inhibitors such inhibitors of metalloproteinases, acid proteases, and thiol proteases, respectively.

21 Claims, 4 Drawing Sheets

USE OF PROTEASE INHIBITORS FOR TREATING SKIN WOUNDS

This application claims the benefit of U.S. Provisional Applications Ser. No. 60/084,682, filed May 7, 1998 and Ser. No. 60/080,315, filed Apr. 1, 1998.

BACKGROUND OF THE INVENTION

The skin acts as the body's first line of defense against infection. Accordingly, it is important that lesions or wounds in the skin must be rapidly closed to prevent infection. Some types of wounds, however, are resistant to healing under normal physiological conditions. For example, chronic ulcers may be defined as wounds that fail to heal. Such ulcers are a common complication of diseases such as diabetes or other pathologies where chronic venous insufficiency occurs. Methods of healing such ulcers have received significant attention recently. See, for example, U.S. Pat. No. 5,693,332 (use of keratinocytes), U.S. Pat. No. 5,646,117 (use of monocyte chemotactic and activating factor, MCAF), U.S. Pat. No. 5,202,118 (use of IL-1), and U.S. Pat. No. 5,599,788 (use of H3 protein), the respective disclosures of which are hereby incorporated by reference in their entireties.

It is apparent, therefore, that improved methods for treating chronic wounds, such as chronic ulcers, are greatly to be desired. In particular, new methods are needed for accelerating healing of chronic wounds.

Previous work has shown that protease activity is increased in chronic wounds. See Palolahti et al., *Exp. Derm.*, 2:29 (1993) and Wysocki et al., *J. Invest. Dermatol.* 101:64 (1993). The present inventors have found that inhibition of this protease activity may be used to treat such chronic wounds.

SUMMARY OF THE INVENTION

It is therefore an object of the present invention to provide improved methods for treating wounds.

It is a further object of the present invention to provide pharmaceutical compositions for use in methods of wound healing.

In accomplishing these objects, there has been provided, in accordance with one aspect of the present invention, a method of treating wounds, comprising administering to a patient in need thereof an effective amount of a therapeutic agent comprising a serine protease inhibitor, where the serine protease inhibitor is topically administered to a wound. In one embodiment, the therapeutic agent comprises a urokinase inhibitor. In another embodiment, the therapeutic agent is selected from the group consisting of plasminogen activator inhibitor 2 (PAI-2), a variant thereof having plasminogen activating inhibitory properties, a derivative of PAI-2, and a variant of a derivative of PAI-2. In still another embodiment, the serine protease inhibitor is administered in a gel formulation. The gel may be a cellulose gel further comprising a detergent. The detergent may be Tween-80.

In accordance with another aspect of the invention there has been provided a method of treating wounds comprising administering to a patient in need thereof an effective amount of a therapeutic agent comprising PAI-2, a variant, derivative, or variant of a derivative of PAI-2, and at least one other serine protease inhibitor, where the therapeutic agent is topically administered to the wound. In one embodiment, the other serine protease inhibitor is a uPA inhibitor. In another embodiment, the therapeutic agent further comprises a protease inhibitor selected from the group consisting of thiol protease inhibitors, acid protease inhibitors, and metalloproteinase inhibitors. In yet another embodiment, the protease inhibitors are co-administered with PAI-2, or a variant, derivative, or variant of a derivative of PAI-2. In still further embodiments, the PAI-2 or variant, derivative, or variant of a derivative of PAI-2 is administered in a range of 0.1–2000 $\mu g/cm^2$ of wound. In another embodiment, the PAI-2 or variant, derivative, or variant of a derivative of PAI-2 is administered at least once a day for at least five days.

In further embodiments, the derivative of PAI-2 is obtained by biochemical modification of PAI-2, where the modification is selected from the group consisting of chemical linking with polyethylene glycol, phosphate group attachment, sulfate group attachment, peptidase treatment, treatment with a sugar chain-modifying enzyme, and treatment with a sugar attachment enzyme. In still other embodiments, a variant of PAI-2 is obtained by deletion or addition of amino acid residues from the amino terminal end of PAI-2. The variant may be obtained by deletion or addition of amino acid residues from the carboxy terminal end of PAI-2.

In accordance with another aspect of the invention there has been provided a pharmaceutical composition comprising PAI-2 or a PAI-2 derivative, variant, or variant of a derivative, in a gel containing a detergent. In one embodiment the detergent is Tween-80, and the gel is a cellulose gel.

In accordance with another aspect of the invention there has been provided a pharmaceutical composition comprising PAI-2 and at least one other serine protease inhibitor. The pharmaceutical composition may further comprise a protease inhibitor selected from the group consisting of thiol protease inhibitors, acid protease inhibitors, and metalloproteinase inhibitors. In another embodiment, the composition is in the form of a cellulose gel that comprises a detergent.

Other objects, features and advantages of the present invention will become apparent from the following detailed description. It should be understood, however, that the detailed description and the specific examples, while indicating particular embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The present invention provides methods and compositions that aid the healing of chronic leg ulcers and other wounds, based on the application of a serine protease inhibitor topically, i.e., to the surface of a wound or ulcer. The skilled artisan will recognize that methods of treating ulcers as described herein also are applicable to treating other skin wounds. In a preferred embodiment, a urokinase plasminogen activator (u-PA) inhibitor is provided as a topical agent.

The invention also encompasses compositions comprising a protease inhibitor in conjunction with another protease inhibitor for treating leg ulcers, and methods for treating the ulcers. Thus, methodology and compositions are provided for treating ulcers and other wounds, where a protease inhibitor is used in combination with one or more other protease inhibitors to provide improved wound healing.

In a preferred embodiment, plasminogen activator inhibitor 2 (PAI-2) is the topical agent. The properties of PAI-2 are described in detail in Kruithof et al., "Biological and Clinical Aspects of Plasminogen Activator Type II," *Blood* 86:4007 (1995), the contents of which are hereby incorporated by reference. Briefly, PAI-2 is a component of the plasminogen activator (PA) system. The PA system has numerous functions, including regulation of extracellular proteolysis in a wide variety of physiological processes, such as tissue remodeling, cell migration, wound healing, and angiogenesis.

Plasminogen activators (PA) are serine proteases that convert plasminogen into plasmin, a trypsin-like serine protease, that is responsible not only for the degradation of fibrin, but also contributes to the degradation and turnover of the extracellular matrix. Plasmin can be formed locally at sites of inflammation and repaired by limited proteolysis of its inactive precursor, plasminogen, which circulates in plasma and interstitial fluids. Plasminogen is activated by either urokinase-type plasminogen activator (u-PA) or tissue-type plasminogen activator (t-PA). These catalytic reactions generally take place at the plasma membrane (u-PA) or on a fibrin surface (t-PA). These activating enzymes are produced by a wide range of mesenchymal, epithelial and endoepithelial cells in response to a variety of cytokines and growth factors. Activated plasmin can degrade a wide range of substrates including extracellular matrix macromolecules (excluding collagens) and fibrin. The activities of plasmin and its activating proteinases are regulated extracellularly through a number of protease inhibitors including PAI-2 and plasminogen activator inhibitor-1 (PAI-1).

The present inventors have found that the topical administration of a compound selected from the category of serine protease inhibitors, such as PAI-2, results in a significant decrease in the area of leg ulcers compared to controls. The skilled artisan will recognize that the use of PAI-2 or other serine protease inhibitors in this fashion is not limited to treatment of leg ulcers, but extends to wound healing in general and to the healing of chronic skin wounds or lesions in particular. Examples of such wounds include surgical or trauma wounds, abrasions, skin tears, blisters, pressure ulcers, diabetic ulcers, venous ulcers, arterial ulcers, mixed ulcers, and burns.

In one aspect of the present invention, the serine protease inhibitor PAI-2 is used. Variants of PAI-2, which substantially have the amino acid sequence of PAI-2 and which inhibit plasminogen activators, also can be used as the effective ingredient in wound healing preparations according to the present invention. That is, a "variant of PAI-2" is a protein having substantially the amino acid sequence of PAI-2, to the extent that residues of the PAI-2 amino acid sequence are deleted, added or substituted, naturally or artificially, but the characteristic inhibitory activity of PAI-2 is not lost. Assays for PAI-2 activity, well known in the art, are readily applicable to the screening of putative variants in this regard.

Thus, conservative, semi-conservative, and other amino acid substitutions are contemplated by the present invention, as long as they do not so reduce activity such that the affected polypeptide is therapeutically ineffective in this context. Sequences in the N-terminal and C-terminal regions of naturally occurring and recombinant PAI-2 may vary—causing an increase or decrease in the number of amino acid residues—depending on the production conditions. These variations specifically are within the scope of the present invention. The skilled artisan will recognize that other active variants of PAI-2 also may be used in the invention, provided that they retain the characteristic protease inhibitor properties of PAI-2.

Also suitable as the active ingredient, pursuant to the present invention, are derivatives that can be produced by chemically or biochemically modifying PAI-2 or a PAI-2 variant. Exemplary of such derivatives are compounds obtained (A) by chemically linking polyethylene glycol or an analogue thereof, (B) by attaching phosphate or sulfate groups, (C) by treatment with a peptidase, such as an endopeptidase, and (D) by treatment with a sugar chain-modifying enzyme or a sugar chain-attaching enzyme, such as sialidase. Derivatives prepared in this fashion can be assayed for protease inhibitor activity by methods that are well known in the art. See, for example, Fersht, ENZYME STRUCTURE AND MECHANISM, 2d ed. W.H. Freeman and Co., 1985, and references therein.

The protease inhibitor, such as PAI-2 or the PAI-2 variants and derivatives described herein (herein collectively referred to as "PAI-2") may be administered topically to patients in any suitable physiologically acceptable vehicle, for example, in phosphate-buffered saline (PBS) solution. Other vehicles are well known in the art and are described, for example, in REMINGTON'S PHARMACEUTICAL SCIENCES, 18th Edition, Mack Publishing Company, Easton, Pa. (1990).

The protease inhibitor can be applied to the wound daily, or more or less frequently as required. The skilled artisan will recognize that optimization of dosage regimens for particular applications is well known in the art, for example as described in REMINGTON'S, supra. A typical daily dosage of inhibitor will be 20 $\mu$g per $cm^2$ of the wound or ulcer, although it will be recognized that this amount may be varied, and concentrations of 0.1–2000 $\mu g/cm^2$ advantageously may be used. For example, ulcers of long duration (such as one year or longer) may require concentrations of 500 $\mu g/cm^2$ applied multiple times per day, such as, for example, 2, 3, or 4 times daily. For ulcers of lesser duration, or those which are responding well to higher doses, the dose may be lowered. For example, the protease inhibitor dose may be lowered sequentially to, for example, 100, 10, 1, or 0.1 $\mu g/cm^2$. In addition, the application of the inhibitor may be made less frequently, such as from 4 to 1 times daily. PAI-2 does not appear to have systemic toxicity and, therefore, even higher doses may be used if necessary. If necessary, the systemic concentration of PAI-2 can be measured using an ELISA test, and the dosage of PAI-2 can be adjusted accordingly. The toxicity and systemic concentration of other suitable inhibitors can be measured by methods known to those of skill in the art.

The concentration of inhibitor in the vehicle used for application to the patient advantageously is about 1 mg/ml, although higher or lower concentrations can be used if necessary. For example, concentrations as low as about 0.1 mg, or as high as the limit of solubility of inhibitor in the vehicle, may be used.

The inhibitor may be applied via short or long term application. Vehicles such as PBS are suitable for short term application of the inhibitor. For longer term application, use of a slow release vehicle is preferred. For example, a gel formulation can be used for effective delivery of the inhibitor. Cellulose derivatives previously have been described to be compatible in gel formulations with certain proteins such as EGF, TGF-α, PDGF and FGF. Proteins in these formulations tend to aggregate over time, however, which is deleterious for the present application. This aggregation is manifested as opalescence or turbidity of the gel, and leads to lower activity of the active protein ingredient, and slower release of the protein from the gel, due to the increased size of the aggregates.

The present inventors have overcome this aggregation problem by the addition of a small amount (up to, and including, 0.05%) of detergent to a inhibitor/cellulose polymer gel. This results in a gel that has substantially improved clarity. The advantages of this gel are shown in more detail in Example 3, infra. Detergents such as Tween 80 or Genapol PF10 may be used. The skilled artisan also will recognize that other detergents may also successfully be used.

Unexpectedly, the present inventors have found that, in addition to reducing aggregation in the gel, use of Tween 80 at 0.02% results in enhanced release of the inhibitor from an inhibitor/Natrosol-containing gel. These experiments are described below in Example 3.

The effect of various protease inhibitors on activity of proteases in wound fluid has been studied. These data are described in more detail in Example 3, infra.

The present inventors have found that only serine protease inhibitors, particularly uPA inhibitors, are capable of high levels of protease inhibition in wound fluid. To achieve these levels of inhibition, the presence of at least one serine protease inhibitor thus is necessary.

Figure 1:
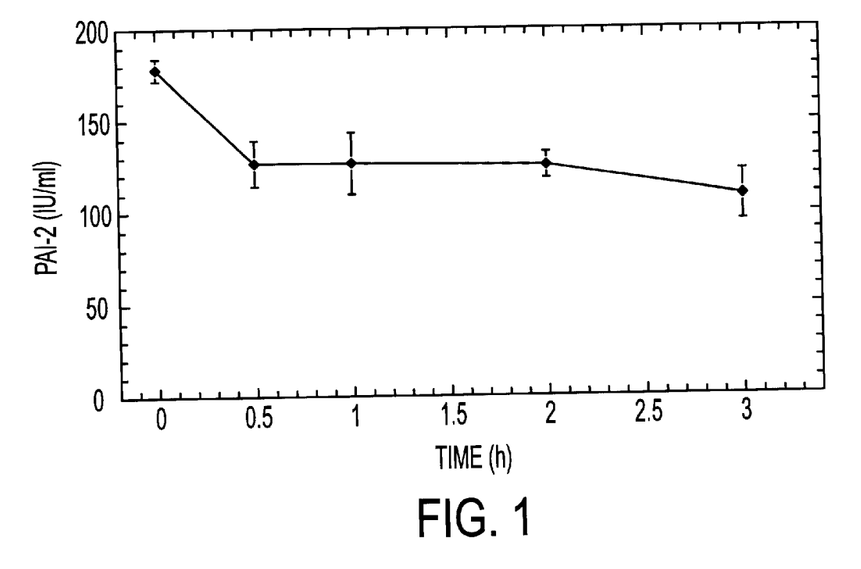
FIG. 1 shows the stability of PAI-2 in wound fluid over a 3-hour period.

It also is apparent that the inhibitors must be stable in the wound fluid to be effective in aiding wound healing. In the context of the present invention, an inhibitor is suitably stable when it retains at least 50% of its activity after exposure to wound fluid for 3 hours. In this regard, therefore, it is particularly desirable to use an inhibitor that inhibits uPA and is stable in wound fluid. It was observed, for example, that addition of PAI-2 to wound fluid caused the inhibition of uPA activity, and also that PAI-2 was relatively stable in wound fluid, as shown in FIG. 1.

By contrast, inhibitors of metalloproteases, acid protease or thiol proteases, when used alone, give much lower amounts of inhibition. See, for example, the data in Example 2, infra. The present inventors have found, however, that the efficacy of a single inhibitor may be enhanced by the use of another inhibitor. These combinations of inhibitors can achieve very high levels of inhibition, for example, inhibition of up to 97% of protease activity. For example, the present inventors have found that the efficacy of PAI-2 may be enhanced by the use of other protease inhibitors in conjunction with PAI-2.

In one embodiment, PAI-2 is used in conjunction with at least one other protease inhibitor. For example, PAI-2 may be used in conjunction with another serine protease inhibitor, such as amiloride, or a derivative thereof.

In another embodiment, PAI-2 is used in conjunction with at least one inhibitor of metalloproteinases, acid proteases and/or thiol proteases. For example, PAI-2 may be used in conjunction with one or more of ethylene diamine tetraacetic acid (EDTA), pepstatin, and N-ethyl maleimide (NEM).

In still another embodiment, PAI-2 is used in conjunction with a combination of at least one other protease inhibitor and at least one other inhibitor of metalloproteinases, acid proteases and/or thiol proteases.

Inhibitors of serine and thiol proteases, and of acid proteases and metalloproteases, are well known in the art, and many are commercially available, for example, from Boehringer Mannheim (Indianapolis, Ind.), Promega (Madison, Wis.), Calbiochem (La Jolla, Calif.), and Life Technologies (Rockville, Md.). Other inhibitors are, described in well-known texts on enzymology, for example, Fersht, ENZYME STRUCTURE AND MECHANISM, 2d ed. W.H. Freeman and Co., 1985, and references therein.

The protease inhibitors may be applied before or after, or simultaneously with, PAI-2 treatment. The inhibitors also may be applied more or less frequently than PAI-2. In particular, inhibitors that are more rapidly degraded may be applied more frequently than more stable inhibitors. Conversely, more stable inhibitors can be applied less frequently. The skilled artisan will recognize that straightforward assays of inhibitor stability may be used to gauge the frequency of administration of the inhibitors.

Advantageously, the protease inhibitors may be applied in the same vehicle as the PAI-2, although this is not essential for efficacy. In particular, the inhibitors may be applied in the same gel vehicle that may be used for PAI-2, as described above. If the inhibitors are not applied in the same vehicle as PAI-2, then they can be applied in any pharmaceutically acceptable vehicle, as described, for example, in REMINGTON'S, supra.

The present invention, thus generally described, will be understood more readily by reference to the following examples, which are provided by way of illustration and are not intended to be limiting of the present invention.

EXAMPLE 1

Use of PAI-2 for Treating Chronic Venous Leg Ulceration

Design

The study was a double blind placebo controlled randomized trial. A stratified randomization was utilized according to ulcer size. Patients with ulcers less than, and greater than, 20 $cm^2$ were randomized separately. No minimum or maximum times were set for the patients' current ulcer episode. Minimum and maximum ulcer areas were 2 $cm^2$ and 50 $cm^2$, and a patient's resting ankle brachial doppler arterial pressure index for inclusion was equal to or greater than 0.80.

All patients received compression bandaging. The area of the ulcer was determined by tracing, and the test solution, either PAI-2 at 1.0 mg/ml in phosphate buffered saline, pH 7.0, or buffer alone, was applied at 20 µl (20 µg in the case of PAI-2) per $cm^2$. The patient was asked to lie recumbent on the examination couch while the test solution was applied to the surface of the wound, and to remain there for 15 minutes before bandaging was applied.

Test solution was applied in this manner for five consecutive days. This was followed by visits on days 15, 22, and 29. Ulcer area determination was made on days 1, 5, 15, 22, and 29, ulcer volume was measured by structured light assessment on days 1, 5, and 29, and the ulcer was photographed on days 1, 5, and 29. Adverse events were assessed at each visit, as were concomitant medications.

In addition, wound fluid was collected on the first day before addition of test solution, and 2 hr, 4 hr, and 6 hr afterwards. Wound fluid collection was also made on days 2, 3, 4, and 5 (before test solution addition) and day 29. Blood samples were taken on day 1 at 0 (before), 0.5 hr, 1 hr, and 2 hr after the test solution, and also at day 5. A punch biopsy was taken for histochemical examination of the ulcer edge on day 5.

All wound fluid samples were analyzed for uPA activity by the Chromolise assay, and for total protein by the Bradford assay. If sufficient wound fluid was available, the following assays were also performed, in order of priority: (i) PAI-2 antigen level, by ELISA; (ii) a Western blot to detect whether the PAI-2 molecule was intact, complexed, or in fragments; (iii) total protease activity, determined by a chromogenic assay using azo-casein as substrate, and (iv) total protease activity in the presence of EDTA (to block metalloproteases) or aprotinin (to block plasmin). In addition, blood samples were analyzed by PAI-2 ELISA (0, 0.5, 1, 2 hr on day 1) and analyzed for FBC and clinical chemistry on day 1(0) and day 5.

The Chromolise uPA assay (BioPool Diagnostic kits, Dade International) was used to measure total uPA, that is both active two-chain uPA and inactive single chain uPA, as the latter is converted to the former by the addition of plasmin in the assay. The ELISA used for PAI-2 detected both glycosylated and non-glycosylated PAI-2, and both complexed (with uPA or tPA) and uncomplexed PAI-2. Insufficient wound fluid was obtained for total protease assays in the presence of aprotinin or EDTA. The variation in ulcer volume measurements by structured light assessment was very large:—20.4% on repeated measurements, so those data could not be used to judge small changes in ulcer volume.

Results

Twenty patients completed the full trial protocol, and one completed the first half of the schedule. Overall, 12 patients were randomized to the PAI-2 group and 9 to the placebo group. The incomplete patient was in the PAI-2 group, and those data were included in uPA analysis over days 1–5, but were excluded from analysis of all other parameters over the complete protocol. Throughout the course of the study 23 adverse events were observed, three of which were regarded as serious. But none of the adverse events was deemed related to the PAI-2 treatment. Accordingly, PAI-2 appeared to be safe for topical use in chronic leg ulcers.

The two groups of patients were comparable with respect to age, sex, duration of ulcer and ulcer volume, but the placebo group had a greater initial ulcer size. When the ulcer areas in the two groups were compared over the 29-day course of the study using the repeated measures analysis of variance, a reduction in the ulcer area in the PAI-2 group was observed, while the placebo group showed no change. The data are shown in the table below:

| | Placebo | | | | |
|---|---|---|---|---|---|
| Patient number | Day I | Day 5 | Day 15 | Day 22 | Day 29 |
| 001 | 7.30 | 7.50 | 7.60 | 6.20 | 5.70 |
| 007 | 14.40 | 11.30 | 12.20 | 12.50 | 13.60 |
| 009 | 7.40 | 6.60 | 7.70 | 6.80 | 8.20 |
| 013 | 7.30 | 8.30 | 8.00 | 10.00 | 11.30 |
| 015 | 10.50 | 8.80 | 9.60 | 8.10 | 5.20 |
| 016 | 3.50 | 2.80 | 3.00 | 2.00 | 2.20 |
| 032 | 34.80 | 32.80 | 39.20 | 43.40 | 39.60 |
| 033 | 44.70 | 43.50 | 43.80 | 44.80 | 44.80 |
| 034 | 22.40 | 17.60 | 18.90 | 16.70 | 24.60 |
| Median | 10.50 | 8.80 | 9.60 | 10.00 | 11.30 |

-continued

| | Placebo | | | | |
|---|---|---|---|---|---|
| Patient number | Day I | Day 5 | Day 15 | Day 22 | Day 29 |
| (IQR) | (7.30, 28.60) | (7.05, 25.20) | (7,65, 29.05) | (6.50, 30.05) | (5.45, 32.10) |

| | PAI-2 | | | | |
|---|---|---|---|---|---|
| Patient number | Day I | Day 5 | Day 15 | Day 22 | Day 29 |
| 002 | 4.50 | 3.80 | 4.10 | 4.10 | 3.70 |
| 003 | 7.10 | 5.20 | 6.00 | 5.30 | 5.00 |
| 004 | 1.80 | 1.10 | 1.10 | 0.90 | 1.20 |
| 005 | 2.60 | 1.10 | 0.60 | 0.30 | 0.30 |
| 006 | 19.80 | 20.10 | 19.50 | 20.90 | 21.50 |
| 008 | 4.90 | 5.20 | 4.80 | 3.90 | 3.80 |
| 010 | 13.30 | 13.20 | 12.60 | 11.50 | 3.30 |
| 011 | 6.60 | 6.40 | 6.90 | 7.70 | 6.80 |
| 012 | 5.10 | 5.60 | 6.40 | | |
| 014 | 2.50 | 1.40 | 1.10 | 0.10 | 0.00 |
| 017 | 3.20 | 3.20 | 2.40 | 2.70 | 3.90 |
| 031 | 38.00 | 36.50 | 25.60 | 26.30 | 24.50 |
| Median | 5.00 | 5.20 | 5.40 | 4.10 | 3.80 |
| IQR | (2.75, 11.75) | (1.85, 11.50) | (1.43, 11.18) | (0.90, 11.50) | (1.20, 6.80) |

(IQR-interquartile range)

Figure 2:
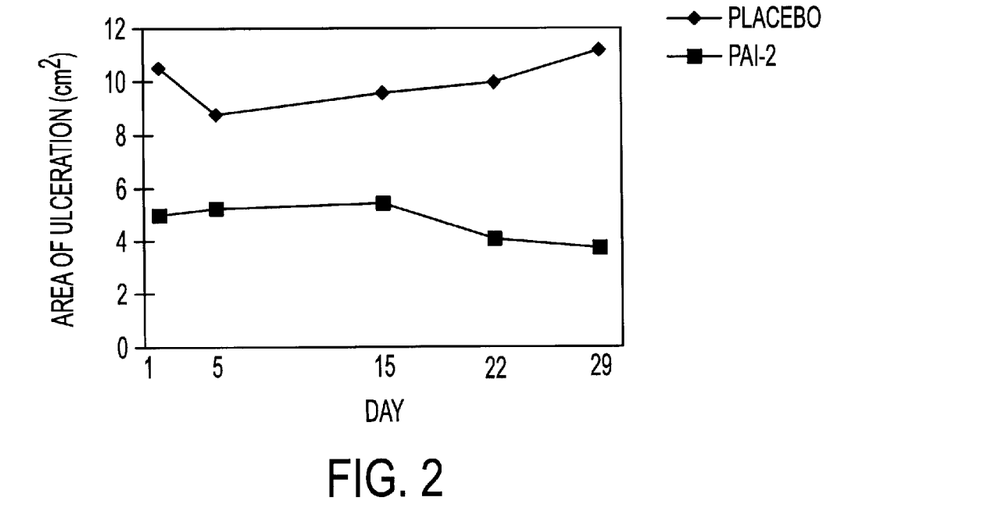
FIG. 2 shows the area of ulceration ($cm^2$) for patients receiving either a placebo (diamonds) or PAI-2 (squares) at various time intervals.

FIG. 2 shows the median area of ulceration of the two groups of patients.

PAI-2 was measured in most patients in wound fluid samples taken at 0, 2, 4, and 6 hrs at the first visit. The level of PAI-2 increased dramatically at 2 hr in those patients receiving the drug, and had declined almost to baseline by 4 hr. Western blot analysis of these samples showed the presence of significant amounts of intact PAI-2 at 2 hr, which indicated that PAI-2 was not being degraded in this time. Consequently, it is believed that most of the PAI-2 not accounted for at 2 hr, and thereafter, probably had been absorbed into the ulcer. No evidence of systemic distribution of the topically applied PAI-2 was found.

Figure 3:
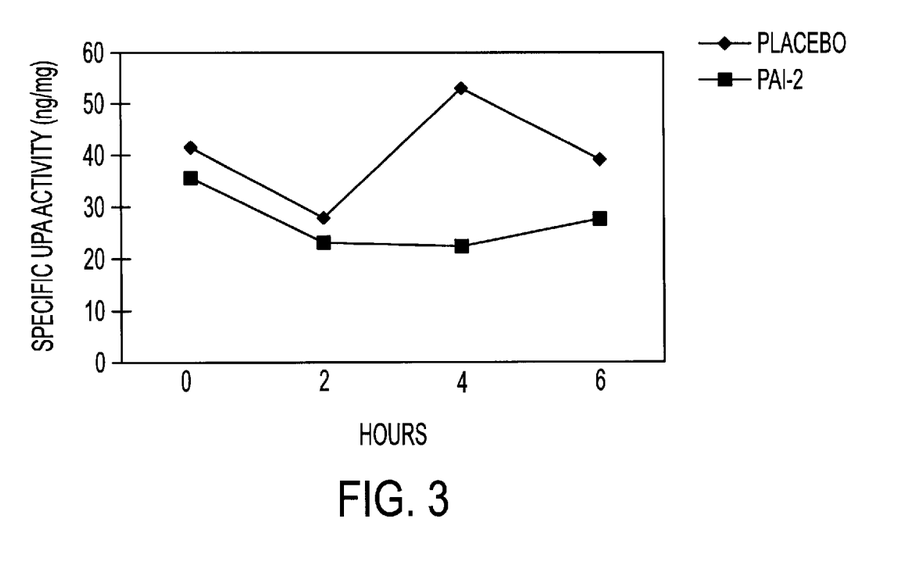
FIG. 3 shows specific uPA activity in patients' wound fluid during the first day of PAI-2 administration.

The specific activity of uPA (ng/mg of total protein in wound fluid) declined over 6 hrs on the first day of PAI-2 administration, relative to the placebo group (see FIG. 3). However, on subsequent days over the course of the study, there was no significant difference in the uPA activity between the two groups, indicating a "rebound" of uPA synthesis after inhibition by PAI-2.

The difference in uPA between the two groups was not apparent when expressed as units/ml of wound fluid, rather than per mg total protein, indicating differences in water content of the wound fluids. This was not a consequence of the addition of PAI-2 protein, which had no significant effect on the total protein levels. On average, 100, μg PAI-2 was added to a 5 cm$^2$ ulcer, while the protein content of wound fluid is approximately 30 mg/ml. Total protease activity did not appear to be altered by the addition of PAI-2, whether measured as ng/ml of wound fluid or as ng/mg protein, although statistical evaluation of a larger study population would be useful to confirm this fact.

Histological examination was performed on biopsies taken at visit 5 after staining with hematoxylin and eosin. No evidence of damage to the tissue was observed from the topical application of PAI-2, and there were very few differences in the histopathological descriptions between the two groups. A somewhat reduced incidence of fibrinoid necrosis in the vessels in the biopsies from patients treated with PAI-2 was observed. This effect is likely to be beneficial to the ulcer.

EXAMPLE 2

Inhibition of Protease Activity in Wound Fluid

Wound fluid was collected from patients with chronic venous leg ulcers, and incubated in vitro in the presence or absence of each inhibitor along with the protease substrate ZGGRAMC. Cleavage of this substrate indicated protease activity, which was detected by fluorescence at 460 nm. Lack of fluorescence indicated inhibition of protease activity.

Inhibition of Protease Activity in Wound Fluid

Single Inhibitors

| Inhibitor | Mode of Action | Percent Inhibition |
|---|---|---|
| EGRCK | uPA (non competitive) | 94 |
| Amiloride | uPA (competitive) | 96 |
| Pepstatin | Acid Protease | 0 |
| EDTA | Metalloproteases | 0 |
| NEM | Thiol proteases | 21 |
| AEBSF | Serine proteases (e.g. uPA, tPA) | 0 |

Key:
EGRCK glutamic acid-glycine-arginine chloromethyl ketone
EDTA ethylene diamine tetraacetic acid
NEM N-ethyl maleimide
AEBSF 4-(2-aminoethyl)-benzene sulphonyl fluoride
ZGGRAMC carbobenzoxy-glycine-glycine-arginine-aminomethyl coumarin.

Multiple inhibitors

| Inhibitor | Percent Inhibition |
|---|---|
| Pepstatin + EDTA | 19 |
| Pepstatin + NEM | 71 |
| Pepstatin + AFBSF | 98 |
| EDTA + NEM | 65 |
| EDTA + AEBSF | 97 |
| NEM + AEBSF | 94 |
| Pepstatin + EDTA + NEM | 60 |
| Pepstatin + EDTA + AEBSF | 98 |
| Pepstatin + NEM + AFBSF | 93 |
| EDTA + NEM + AFBSF | 90 |
| Pepstatin + EDTA + NEM + AEBSF | 95 |

Conditions were as described above for single inhibitors.

EXAMPLE 3

Preparation of PAI-2-Containing Gels and Measurement of PAI-2 Release

In these experiments, the PAI-2 containing gel was placed in the top chamber of a two compartment vessel. The bottom chamber contained buffer, and the two chambers were separated by a microporous membrane. The appearance of PAI-2 in the lower chamber indicated PAI-2 release from the gel, and was monitored by assays for PAI-2 activity.

Figure 4:
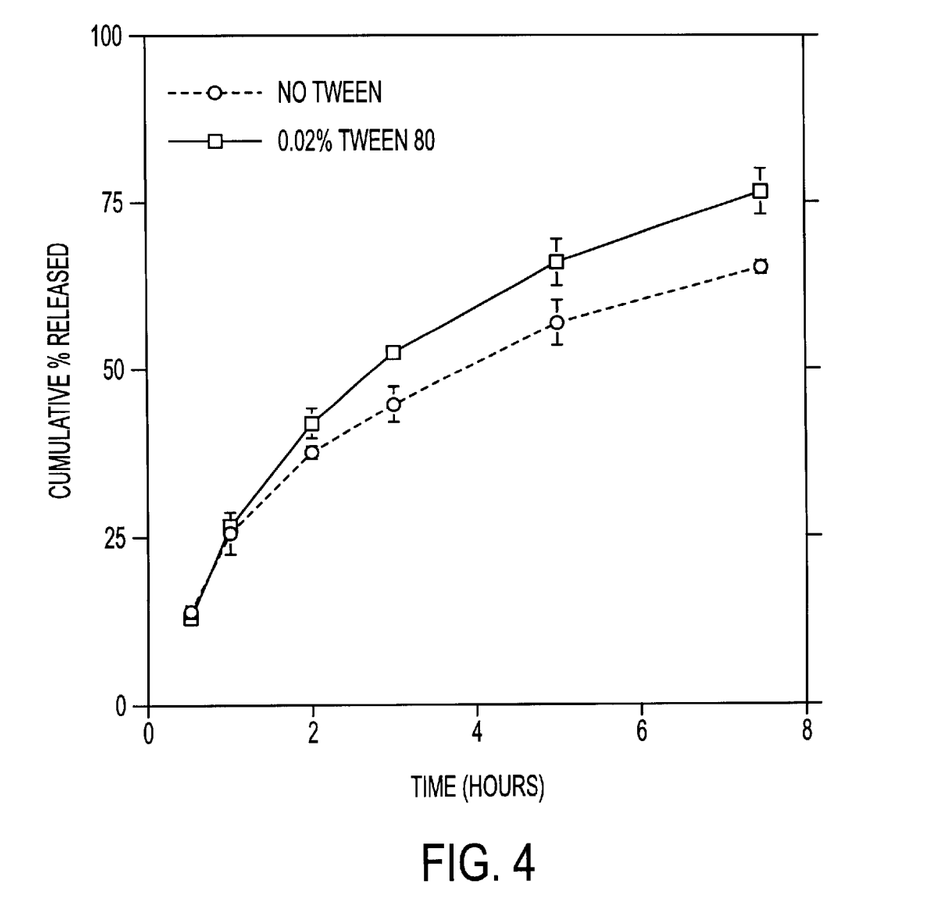
FIG. 4 shows the enhanced release of PAI-2 from a cellulose gel in the presence of Tween80.

The table below reflects the improved properties of the new PAI-2 gel formulations. The enhanced released of PAI-2 from the gel is depicted in FIG. 4.

CLARITY OF PAI-2 GEL FORMULATIONS

| Polymer | Conc. (%) | Excipients Placebo | None | Genapol PFIO | Tween 80 |
|---|---|---|---|---|---|
| Carbopol 971P | 0.5 | clear | s.o. | clear | clear |
| | 1.0 | clear | s.o. | clear | clear |
| Carbopol 974P | 0.5 | clear | opal | s.o. | s.o. |
| | 1.0 | clear | cloudy | opal. | s.o. |
| Carbopol 981 | 0.5 | clear | s.o. | clear | clear |
| | 1.0 | clear | s.o. | clear | clear |
| Blanose 7LF | 2.0 | clear | cloudy$^d$ | v.o.$^d$ | opal. |
| Natrosol 250HHX | 1.5 | clear | s.o. | clear | clear |
| Keltrol RD | 3.0 | opal. | cloudy | v.o. | cloudy |

Key:
opal. = opalescent
s.o. = slightly opalescent
v.o. = very opalescent
$^d$ = possible microbial contamination Methods Polymers were dissolved to the desired concentration, and then titrated to pH 7.4–7.7. Detergents were added to 0.05% and PAI-2 to 1 mg/ml. Sodium azide (0.05%) was used as a preservative.

The invention has been disclosed broadly and is illustrated by reference to representative embodiments described above. Those skilled in the art will recognize that various modifications can be made to the present invention without departing from the spirit and scope thereof.

What is claimed is:

1. A method of treating a chronic skin wound, comprising administering to a patient in need thereof an effective amount of a urokinase inhibitor, wherein said chronic skin wound is selected from the group consisting of pressure ulcers, diabetic ulcers, venous ulcers, arterial ulcers, and mixed ulcers and wherein said serine protease inhibitor is topically administered to said wound.

2. The method according to claim 1, wherein said urokinase inhibitor is selected from the group consisting of PAI-2, a variant thereof having plasminogen activating inhibitory properties, a derivative of PAI-2, and a variant of said derivative.

3. The method according to claim 1, wherein said urokinase inhibitor is administered in a gel formulation.

4. The method according to claim 3, wherein said gel is a cellulose gel further comprising a detergent.

5. The method according to claim 4, wherein said detergent is Tween-80 or Poly(oxyethylene, oxypropylene)glycol 1800.

6. A method of treating a chronic skin wound, comprising administering to a patient in need thereof an effective amount of a therapeutic agent comprising urokinase inhibitor and at least one other protease inhibitor, wherein said chronic skin wound is selected from the group consisting of pressure ulcers, diabetic ulcers, venous ulcers, arterial ulcers, and mixed ulcers and wherein said therapeutic agent is topically administered to said wound.

7. A method according to claim 6, wherein said urokinase inhibitor is PAI-2.

8. The method according to claim 6 wherein said protease inhibitor is selected from the group consisting of serine protease inhibitors other than a urokinase inhibitor, thiol protease inhibitors, acid protease inhibitors, and metalloproteinase inhibitors.

9. The method according to claim 8, wherein said protease inhibitors are co-administered with the urokinase inhibitor.

10. A pharmaceutical composition comprising PAI-2 in a gel containing a detergent.

11. A pharmaceutical composition according to claim 10, wherein said detergent is Tween-80 or Poly(oxyethylene, oxpropylene)glycol 1800, and said gel is a cellulose gel.

12. A pharmaceutical composition comprising PAI-2 and at least one other serine protease inhibitor.

13. A pharmaceutical composition according to claim 12 further comprising a protease inhibitor selected from the group consisting of thiol protease inhibitors, acid protease inhibitors, and metalloproteinase inhibitors.

14. A pharmaceutical composition according to claim 12, wherein said composition is in the form of a cellulose gel that comprises a detergent.

15. The method of claim 2, wherein said PAI-2 is administered in a range of 0.1–2000 $\mu$g/cm$^2$ of wound.

16. The method according to claim 15, wherein said PAI-2 is administered at least once a day for at least five days.

17. The method of claim 2, wherein said derivative thereof is obtained by biochemical modification of PAI-2, wherein said modification is selected from the group consisting of chemical linking with polyethylene glycol, phosphate group attachment, sulfate group attachment, peptidase treatment, treatment with a sugar chain-modifying enzyme, and treatment with a sugar attachment enzyme.

18. The method of claim 2, wherein said variant is obtained by deletion or addition of amino acid residues from the amino terminal end of PAI-2.

19. The method of claim 2, wherein said variant is obtained by deletion or addition of amino acid residues from the carboxy terminal end of PAI-2.

20. The methods according to claim 4, wherein said detergent is added with an amount of up to and including 0.05%.

21. The pharmaceutical composition according to claim 10, wherein said detergent is added with an amount of up to and including 0.05%.

* * * * *